United States Patent
Cao et al.

(10) Patent No.: US 12,336,765 B2
(45) Date of Patent: Jun. 24, 2025

(54) RAY-FREE DENTAL X-RAY PERIAPICAL FILM VIRTUAL IMAGING METHOD BASED ON VIRTUAL REALITY

(71) Applicant: NANJING UNIVERSITY, Jiangsu (CN)

(72) Inventors: Xun Cao, Jiangsu (CN); Yidi Zhang, Jiangsu (CN); Hao Zhu, Jiangsu (CN); Zhuoyi Liao, Jiangsu (CN); Weibin Sun, Jiangsu (CN)

(73) Assignee: NANJING UNIVERSITY, Jiangsu (CN)

( * ) Notice: Subject to any disclaimer, the term of this patent is extended or adjusted under 35 U.S.C. 154(b) by 828 days.

(21) Appl. No.: 17/628,694

(22) PCT Filed: Jul. 14, 2020

(86) PCT No.: PCT/CN2020/101916
§ 371 (c)(1),
(2) Date: Jan. 20, 2022

(87) PCT Pub. No.: WO2021/017819
PCT Pub. Date: Feb. 4, 2021

(65) Prior Publication Data
US 2022/0265356 A1     Aug. 25, 2022

(30) Foreign Application Priority Data

Jul. 29, 2019   (CN) .......................... 201910687262.2

(51) Int. Cl.
*G09B 23/28*     (2006.01)
*A61B 1/06*      (2006.01)
(Continued)

(52) U.S. Cl.
CPC ............ *A61B 34/10* (2016.02); *A61B 1/0605* (2022.02); *A61B 6/032* (2013.01); *A61B 6/51* (2024.01);
(Continued)

(58) Field of Classification Search
CPC .... G09B 23/28; G09B 23/283; G09B 23/285; A61B 34/10
(Continued)

(56) References Cited

U.S. PATENT DOCUMENTS 10,278,584 B2 *   5/2019   Glinec ............... A61B 1/00055
11,534,272 B2 *  12/2022   Li .......................  A61C 9/0053
(Continued)

FOREIGN PATENT DOCUMENTS

CN    108389488 A    8/2018
CN    108665533 A   10/2018
(Continued)

OTHER PUBLICATIONS

Xiao, Yong; "Design of a Surgical Simulator for Root Canal Preparation Training Based on Virtual Reality"; Chinese Master's Theses Full-text Database; Medical and Health Sciences; No. 4; Apr. 15, 2018; ISSN: 1674-0246; pp. 17-51.

*Primary Examiner* — Kurt Fernstrom
(74) *Attorney, Agent, or Firm* — NKL Law; Allen Xue

(57) ABSTRACT

A ray-free dental X-ray periapical film virtual imaging method based on virtual reality (VR) includes: constructing a VR positioning system, and tracing a position of a tracker bonded bound with a tube of a dental film machine and a spatial attitude matrix in real time; scanning and reconstructing a digital three-dimensional (3D) model of dentition; respectively setting different materials and transparency for a shell of a tooth model and an internal pulp cavity; constructing a virtual environment of a simulated oral cav- (Continued)

ity; assigning an attitude and position of the tracker to a virtual camera by using a network communication module, and controlling the virtual camera to move; placing the tracker in a specific position and orientation to calibrate so as to obtain a position coordinate of a dentition model in the virtual environment; and aligning the tube to teeth, and rendering a virtual periapical film.

6 Claims, 4 Drawing Sheets

(51) Int. Cl.
| | |
|---|---|
| *A61B 6/03* | (2006.01) |
| *A61B 6/51* | (2024.01) |
| *A61B 34/10* | (2016.01) |
| *G06T 19/00* | (2011.01) |
| *A61B 34/20* | (2016.01) |

(52) U.S. Cl.
CPC ...... *G06T 19/003* (2013.01); *A61B 2034/104* (2016.02); *A61B 2034/107* (2016.02); *A61B 2034/2055* (2016.02)

(58) Field of Classification Search
USPC .......................................................... 434/263
See application file for complete search history.

(56) References Cited

U.S. PATENT DOCUMENTS

| | | | |
|---|---|---|---|
| 2015/0049081 A1* | 2/2015 | Coffey | A61B 34/10 |
| | | | 345/419 |
| 2017/0065379 A1* | 3/2017 | Cowburn | A61C 13/0004 |
| 2017/0202483 A1* | 7/2017 | Sorimoto | A61B 5/4547 |
| 2018/0110590 A1* | 4/2018 | Maraj | G06T 19/20 |
| 2018/0168780 A1 | 6/2018 | Kopelman et al. | |
| 2021/0251729 A1* | 8/2021 | Schneider | A61C 13/0004 |
| 2022/0008175 A1* | 1/2022 | Öjelund | G06N 20/20 |

FOREIGN PATENT DOCUMENTS

| | | |
|---|---|---|
| CN | 109035386 A | 12/2018 |
| CN | 110458941 A | 11/2019 |

* cited by examiner

RAY-FREE DENTAL X-RAY PERIAPICAL FILM VIRTUAL IMAGING METHOD BASED ON VIRTUAL REALITY

TECHNICAL FIELD

The present invention belongs to the field of Virtual Reality (VR), and specifically, to a ray-free dental x-ray periapical film virtual imaging method based on virtual reality.

BACKGROUND

VR is to generate a digital environment that is highly similar to a certain range of real environments in terms of sight, hearing, and touch by taking a computer technology as a core, and combining sensor systems, graphic and image recognition and generation systems, and network communication systems. Therefore, with necessary devices, users can experience the feeling and experience of being in the real environment. With the development of the computer technology, the VR technology has begun to play a role in many fields, such as the field of virtual simulation. Currently, many skills training such as electrical and electronic training, fire safety, disaster management, construction, medical care, and the like face the following disadvantages: costs are high; steps are complex; the training is not easy to repeat; and during training, there may be a threat to life and health. However, the VR technology can simulate the real environment through modeling, so that the above processes can be performed safely, efficiently and repeatedly without loss. The application of the VR technology in medical treatment mainly includes virtual operation, remote medical systems, virtual human, medical education, and so on.

In the assessment of the conventional oral periapical film, since the device does not emit rays, students can only place a ray emitter in an estimated position according to an external marker point, and no X-ray images are generated, so that teachers can only determine whether the students can obtain correct periapical films according to a placing position of the device and personal experience. As a result, the learning efficiency of the students and the reliability of the assessment are low.

At present, dental diagnosis and treatment simulation systems combined with VR are mainly classified into the following categories.

The first category is a system for periodontal disease diagnosis and treatment, such as a simulator PerioSim developed by the University of Illinois. The system simultaneously takes into consideration of the simulation of hard and soft tissue. A periodontal operation is completed with tactile and force feedback. Therefore, the teachers can score the operations of the students visually.

The second category is a system for oral implantology, such as a Nobel Guide system developed by Nobel bioeare, Sweden, a Simplant system developed by Kusumoto N et al., Belgium and the like. The system is configured to train the students to perceive the feel of preparing holes by a planter, so as to grasp positions and angles of implants in a three-dimensional (3D) direction. A 3D reconstruction model of the jaw of a patient generated based on CT scanning data can be rotated in all directions or even carefully observed on any cross sections, so as to select the optimal position to plant the implant and decide the type, quantity, size, depth and direction of the implant.

The third category is a simulation system for the field of oral and maxillofacial surgery, such as a Simplant system developed by Materials, Belgium. The system includes a 3D structure and a soft tissue structure of the cranio-maxillofacial bone, and can perform some surgical operations in a virtual environment. Most of the conventional surgical simulators use tactile simulation principles similar to those mentioned above, which can simulate bone cutting, osteotomy, bone displacement and postoperative prediction.

The fourth category is a simulation system for diagnosis and treatment of dental pulp diseases, such as a Simodont digital virtual simulation stomatologist training system developed by Moog, America. The operation of the system also involves simulation force rendering and interaction. A virtual tool and teeth are composed of a triangular network data structure. When a triangular plate of a tool cutting end intersects a triangular plate of a tooth surface, and the removing amount of tissue is calculated according to the embedded depth of the tool, thereby realizing deformation simulation of tooth tissue removal.

However, the above methods have at least the following disadvantages: the methods are concentrated on the simulation of touch and force, the reconstructed 3D structure are surface information of objects, the simulation of dental X-ray films is not involved, and a problem that dental X-ray images are unable to be rendered in the assessment of the conventional oral periapical film cannot be resolved.

SUMMARY

In order to generate a dental X-ray periapical film without radiation, the present invention provides a virtual reality (VR) based virtual imaging method of a ray-free dental X-ray periapical film.

In order to implement the above objective, the present invention uses the following technical solutions.

A VR based virtual imaging method of a ray-free dental X-ray periapical film is provided, including the following steps.

S1: VR hardware is used to construct a spatial positioning system, herein the positioning system includes a base station and a tracker, a dental film machine is disposed within a visible range of the positioning system, and the tracker is fixed on a tube of the dental film machine and may implement a tracing function without a head mounted display; and an attitude matrix and position data of the tracker are acquired.

S2: scanning a plurality of teeth, and reconstructing a three-dimensional (3D) digital model of dentition; and segmenting the 3D digital model to respectively acquire a tooth shell model and a pulp cavity model, then forming the two models into a preform, and setting corresponding translucent materials respectively for the two models according to actual tooth structural characteristics;

S3: A virtual imaging environment for photographing a dental periapical film is constructed, a plurality of planes and cylinders are added around the teeth to simulate a background in a dental X-ray film, a size of a bounding box of the 3D digital model of dentition and a size of a bounding box of a dentition model in the real world are measured, and the ratio between the two sizes is calculated; and sizes of the tooth shell model and the pulp cavity model in the virtual imaging environment are adjusted, and reasonable positions and orientations are set for lights and a virtual camera.

S4: in view of the attitude matrix and the position data of the tracker acquired in step S1, converting the attitude matrix into an Euler angle, and then assigning, by means of a network communication module, along with the position data, to the virtual camera in real time, and replacing the virtual camera with the tracker;

S5: The tube is placed right in front of the teeth, the teeth are aligned, a physical distance between the tooth in the middle of dentition and the tracker is measured, and a position of the 3D digital model of dentition in the virtual environment is calibrated according to a position of the tracker and aligned with the real world.

S6: A position and an orientation of the tube are adjusted, and a corresponding virtual dental X-ray periapical film is rendered.

Further, in step S1, the positioning system uses two base stations. The two base stations are placed facing each other and front screens are parallel. One of the base stations is used as an original point of a world coordinate system of the positioning system. The dental film machine is placed between the two base stations. A head mold in the dental film machine faces the base station used as the original point of the world coordinate system. A Y axis of the tracker is parallel to a long axis of the tube and points to the head mold.

Further, in step S2, the teeth are scanned by using a Micro-Computer Tomography (Micro-CT) or Cone Beam Computer Tomography (CBCT) technology.

Further, in step S2, a tooth model includes dental pulp and enamel. A material of the tooth shell model is set to be white. A material of the pulp cavity model is set to be black.

Further, in step S3, the plurality of planes are added around the teeth to surround the teeth, and only a front opening is left to simulate an environment of an oral cavity.

Further, in step S4, the assignment of the acquired attitude matrix and the position data of the tracker is completed by using a publish-subscribe model. A port for acquiring the attitude matrix and the position data of the tracker is used as a publisher. A port where the virtual camera is located is used as a subscriber.

Compared with the prior art, the present invention has the following significant advantages. By combining the VR hardware and the dental film machine, the virtual imaging environment corresponding to the real world is established, so that the position and the attitude of the tube of the dental film machine can be acquired in real time, and the position of a 3D model of the virtual world is calibrated. The camera in the virtual world is controlled to move through the efficient network communication, so that the dental film machine can render the corresponding virtual dental X-ray periapical film without radiation. In this way, the problem that there is no images generated in the training and assessment of the conventional oral periapical film and the positions are hard to determine can be resolved. Therefore, determination evidence is provided for the assessment of the periapical film without radiation, and the visuality and accuracy of the process are improved, so as to cause the process to be safe, efficient, loss-free and repeatable.

DETAILED DESCRIPTION OF THE EMBODIMENTS

In order to make objectives, technical solutions, and advantages of the embodiments of the present invention clearer, the implementation method of the present invention will be clearly and completely described below with reference to the drawings.

Figure 1:
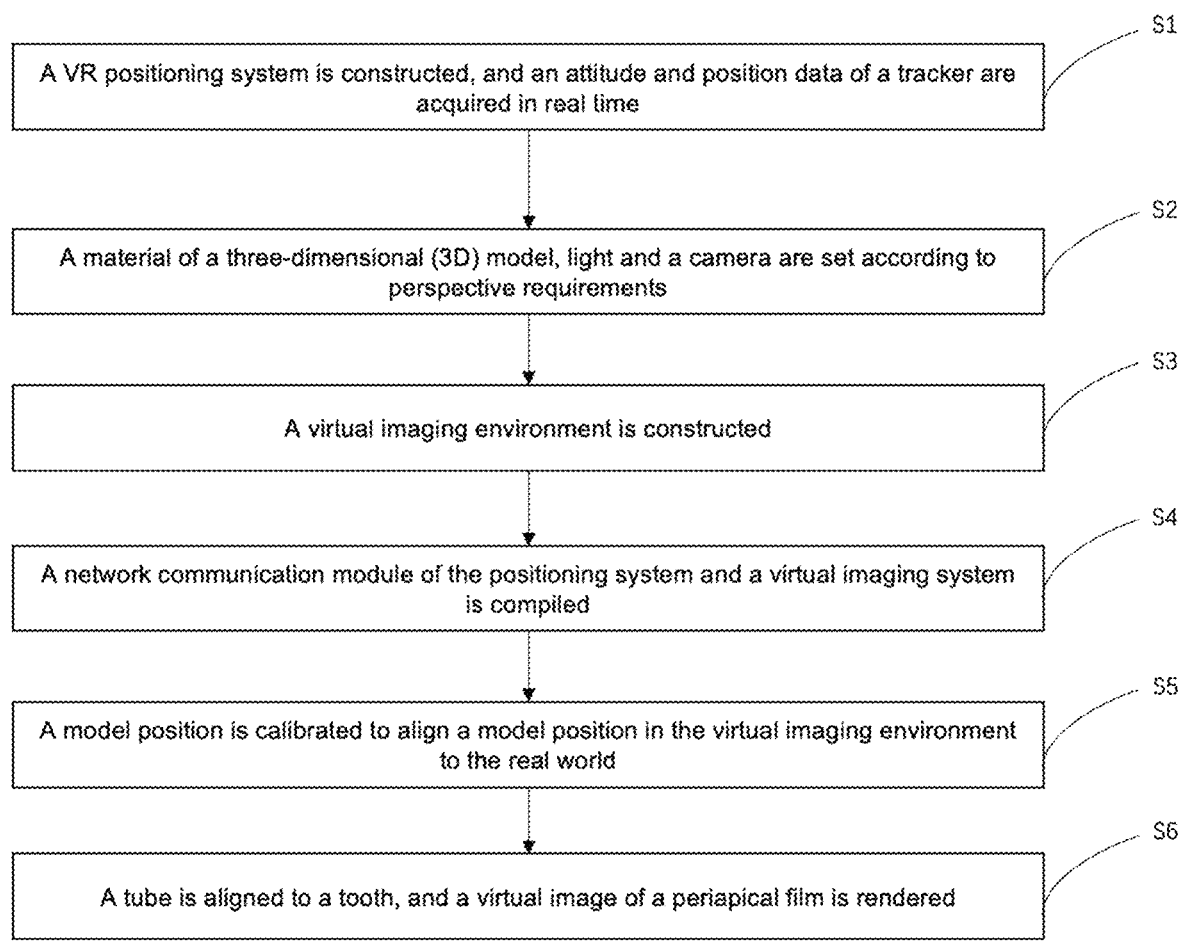
FIG. 1 is a flowchart of a virtual imaging method according to an embodiment of the present invention.

As shown in FIG. 1, a virtual reality (VR) based virtual imaging method of a ray-free dental X-ray periapical film according to this embodiment has the following specific processes.

(1) A Micro-CT technology is used to scan a dentition model formed by a plurality of isolated teeth, to reconstruct a three-dimensional (3D) digital model of dentition. The Micro-CT is specially used for scanning and reconstructing objects with small sizes, so that it is small in scale and high in resolution. An imaging pixel size of a sample may be as small as 100 nanometers, and the objects can be scanned up to 200 millimeters in diameter. In addition to the reconstructed dentition model, an internal pulp cavity structure is further included to facilitate the follow-up perspective rendering.

The digital dentition 3D model acquired herein may further be scanned by a conventional CBCT. The pixel of the conventional CBCT can reach 0.125 mm. The maximum resolution can reach a reconstruction speed of 2.0 lp/mm. The reconstruction time is less than 15 s. An imaging range is reasonable. A 3D image of whole oral cavity and double dentition can be obtained through one scanning. The scanning resolution of the conventional CBCT is slightly lower than the Micro-CT, so that, in the case of low virtual imaging quality requirements, the conventional CBCT can be used to replace the Micro-CT.

(2) An HTC Vive base station and tracker are used to construct a positioning system. The positioning system includes two base stations and one tracker. The two base stations are disposed on a tripod, and placed facing each other with a height being 2 m and a distance being about 4 m. A channel of the base station A is set to "b". A channel of the base station B is set to "c", and the base station B is used as an original point of a world coordinate system of the positioning system. A dental film machine is placed between the two base stations. A head mold faces the base station B. The HTC Vive tracker is fixed on an upper surface of a tube. A Y axis of the tracker is parallel to the tube, and a positive direction of the Y axis points to the head mold. A require Hmd option in a steamVR software default configuration file is changed from true to false. An openVR is used to read an attitude and coordinate of the HTC Vive tracker.

Herein, distances and heights of the base stations may further be adjusted flexibly according to situations, as long as the tracker is guaranteed to be in the fields of view of the base stations.

(3) The 3D digital dentition model obtained in step (1) is imported into 3D animation modeling software Blender to perform segmentation process, so that a tooth shell model and a pulp cavity model are respectively obtained and exported as a .fbx model. Then, the model is made into a preform in Unity. A tooth body is composed of enamel, dentin, dental pulp and cementum. The color of each tissue is different. In this embodiment, a tooth model is simplified into dental pulp and enamel. Since a pulp cavity in a dental X-ray film is black and other parts are white, different materials are respectively set for the pulp cavity and a shell. The material of the pulp cavity is black, and the material of the shell is white. The transparency of the black material is lower than the transparency of the white material. Therefore, a perspective effect of a periapical film can be simulated reasonably.

Figure 2:
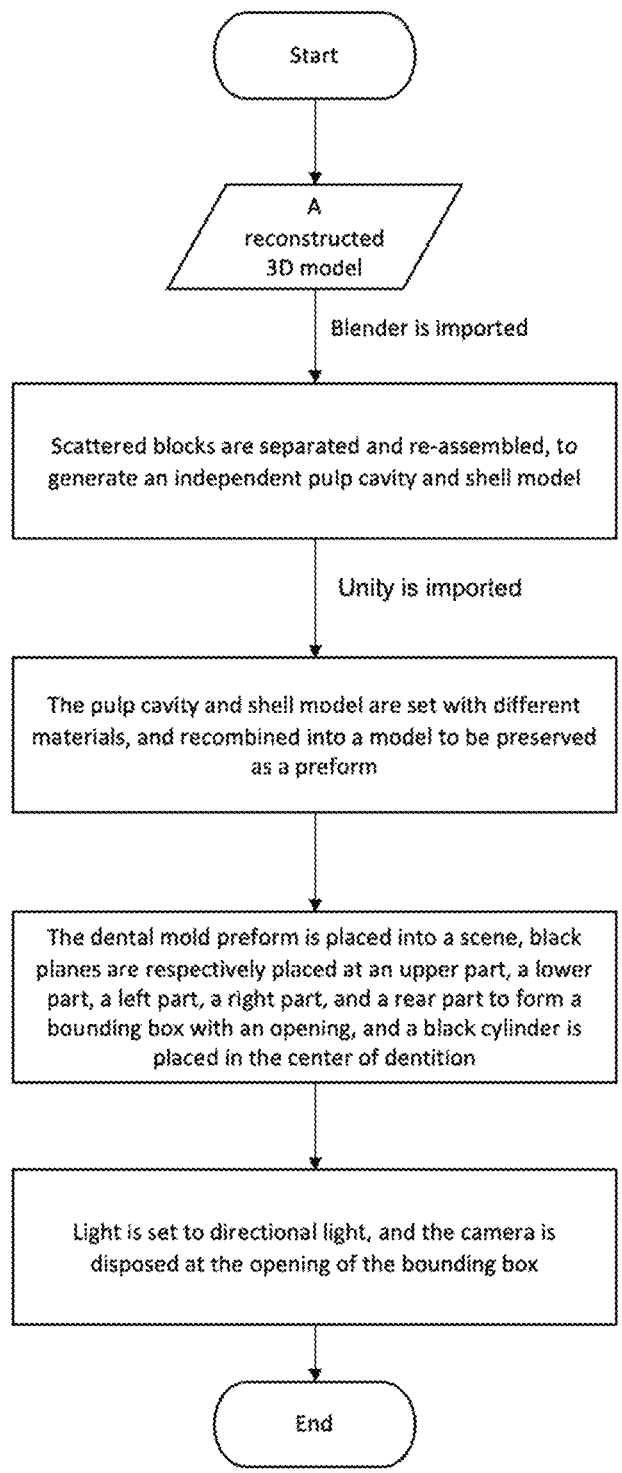
FIG. 2 is a flowchart showing the construction of a virtual environment according to an embodiment of the present invention.

(4) A virtual imaging environment for photographing a dental periapical film is constructed in the Unity. A plurality of black opaque planes are added around the teeth as a background of the dental X-ray film. Black opaque cylinders are added in the middle of dentition. In this way, the backteeth on the other side are prevented from being photographed due to a direction of the dental arch during the photographing of the backteeth. A size of a bounding box of the digital dentition model and a size of a bounding box of a dentition model in the real world are measured, and a ratio is adjusted to be 1:1. Light uses directional light to simulate daylight. A design procedure is shown in FIG. 2.

Herein, when a black background plane is not added, a same rendering effect may also be achieved by merely setting the Clear Flags of a virtual camera as a Solid Color mode. However, the background may be transparent when an image is saved. Therefore, the black plane is added as the background.

Figure 3:
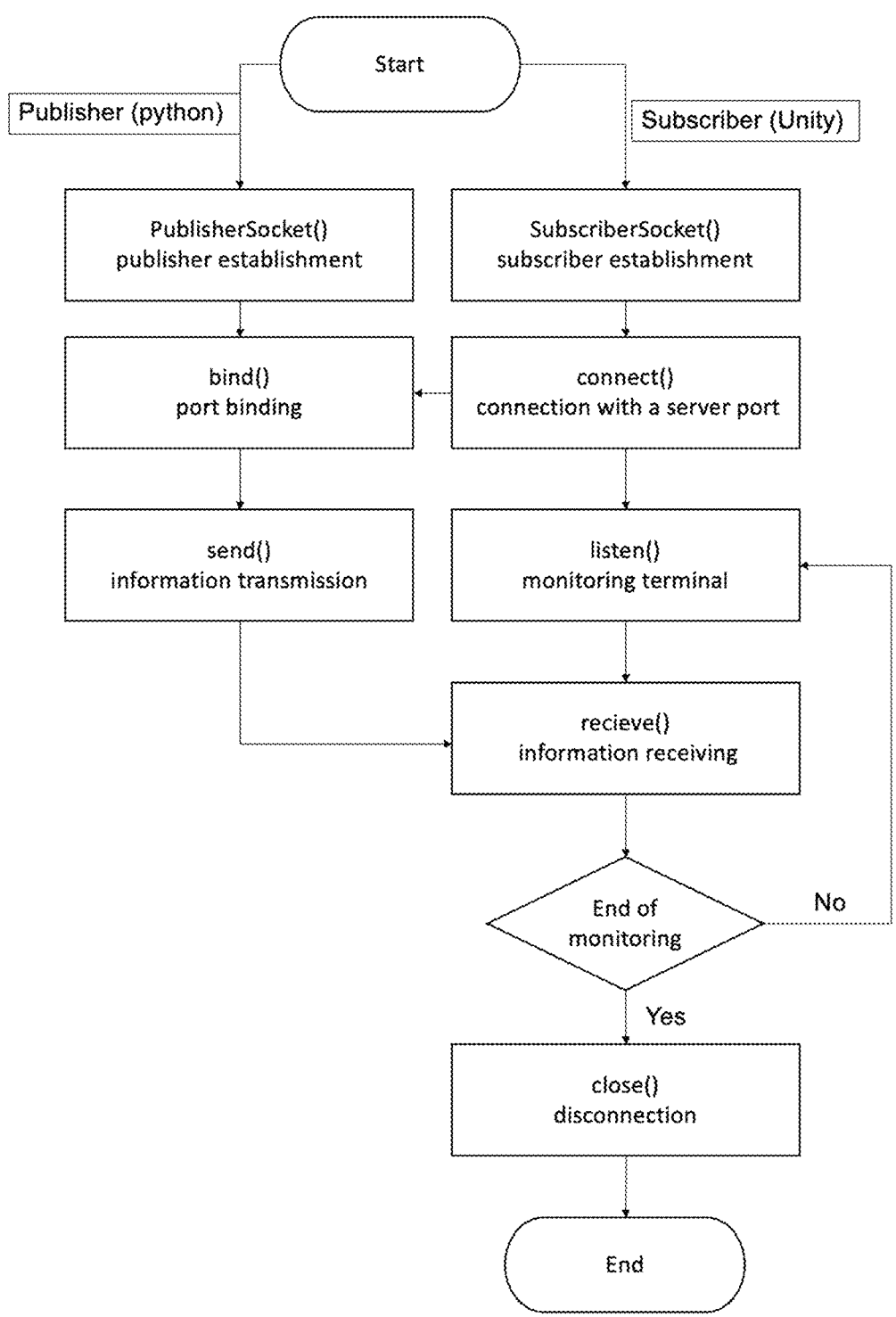
FIG. 3 is a flowchart showing network communication according to an embodiment of the present invention.

(5) The attitude matrix of the HTC Vive tracker read in step (2) is converted into an Euler angle. A publisher-subscriber mode of ZeroMQ is used to complete a data distribution process. The data acquired in step (2) is used as the publisher, and the Unity is used as the subscriber. The publisher distributes the data in one direction, and does not care whether all information is transmitted to the subscriber. If the publisher starts to publish information, and the subscriber is not connected yet, the information is directly discarded. The subscriber is only responsible for receiving, not feedback. When a consumption speed of the subscriber is slower than that of the publisher, the data is accumulated at the subscriber. As a result, the publisher may continuously transmit the data during operation, and in this case, the subscriber does not receive the data. Only when a Unity program is operated, the subscriber may start to receive the data. A zmq module of Python is used to complete the publisher of communication. A local port is bound on the publisher, so that the Euler angle and the position data of the tracker are continuously transmitted through the port. A NetMQ module of C# is used to complete the subscriber of communication. A port is connected to and monitored by the subscriber. A value is assigned to a camera after a message is received. A specific communication procedure is shown in FIG. 3.

(6) The tube is placed right in front of the teeth of the head mold, points to the middle part of dentition and parallelly aligns to the teeth. X and Y coordinates of the teeth and the tube are the same, only values of Z-axis coordinates are different. A physical distance L between the middle tooth and the tracker is measured, which is usually in a range of 25 to 35 cm. According to a position (a, b, c) (cm) of the tracker, a position of the tooth in the Unity is calibrated as (a, b, −c-L), which aligns to the real world. Meanwhile, the ambient environment (including various planes and cylinders) of the dentition model also needs to be transformed in the same way, to guarantee the background is correct when the image is rendered and saved. A coordinate unit of the VR positioning system is m, and is converted into cm in the same way. According to a placing orientation of the dental film machine and a placing orientation of a positioner, the coordinate of the VR positioning system is converted to a coordinate system of the Unity.

Figure 4:
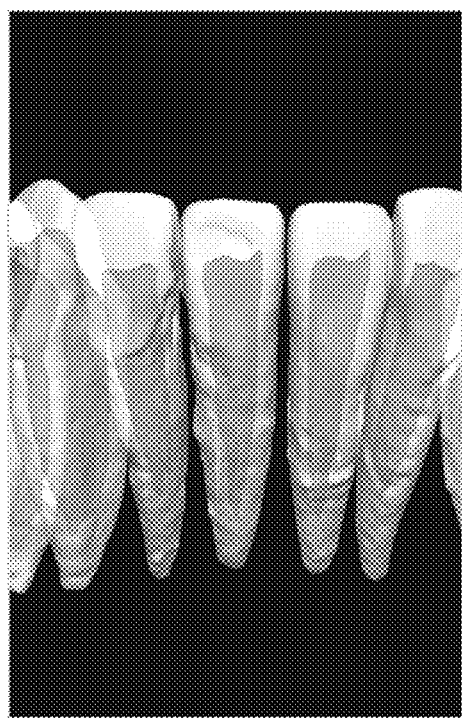
FIG. 4 is a rendering result diagram according to an embodiment of the present invention.

(7) The angle of view of the camera is adjusted, so that the quantity of teeth shown in the view is less than 6, which is consistent to a real dental X-ray film. The tube of the dental film machine is placed to an appropriate position, and aligned to the tooth. A button is pressed to refresh a screen, and the corresponding virtual dental X-ray periapical film is rendered. A rendering result is shown in FIG. 4.

Therefore, in this embodiment, by establishing the virtual environment and imaging conditions of the digital teeth, and using the VR positioning system, the method of the present invention can simulate a process of photographing a dental X-ray periapical film and render a corresponding image without radiation, so that the safety, visuality and accuracy in the assessment of the dental X-ray periapical film are improved.

The invention claimed is:

1. A ray-free dental X-ray periapical film virtual imaging method based on virtual reality (VR), comprising the following steps:

S1: using VR hardware to construct a spatial positioning system, wherein the positioning system comprises a base station and a tracker, a dental film machine is disposed within a visible range of the positioning system, and the tracker is fixed on a tube of the dental film machine and is able to implement a tracing function without a head mounted display; and acquiring an attitude matrix and position data of the tracker;

S2: scanning a plurality of teeth, and reconstructing a three-dimensional (3D) digital model of a dentition; and segmenting the 3D digital model to respectively acquire a tooth shell model and a pulp cavity model, then forming the two models into a preform, and setting corresponding translucent materials respectively for the two models according to actual tooth structural characteristics;

S3: constructing a virtual imaging environment for photographing a dental periapical film, adding a plurality of planes and cylinders around the teeth to simulate a background in a dental X-ray film, measuring the size of a bounding box of the 3D digital model of the dentition and the size of a bounding box of a dentition model in the real world, and calculating the ratio between the two; and adjusting the sizes of the tooth shell model and the pulp cavity model in the virtual imaging environment, and setting reasonable positions and orientations for light and a virtual camera;

S4: for the attitude matrix and the position data of the tracker acquired in step S1, converting the attitude matrix into an Euler angle, and then assigning, by means of a network communication module, same along with the position data, to the virtual camera in real time, and replacing the virtual camera with the tracker;

S5: placing the tube right in front of the teeth, aligning same with the teeth, measuring a physical distance between the tooth in the middle of the dentition and the tracker, and calibrating the position of the 3D digital model of the dentition in the virtual environment according to the position of the tracker at this time so as to align with the real world; and S6: adjusting the position and orientation of the tube, and rendering a corresponding virtual dental X-ray periapical film.

2. The ray-free dental X-ray periapical film virtual imaging method based on VR according to claim 1, characterized in that, in step S1, the positioning system uses two base stations, the two base stations are placed facing each other and front screens are parallel, one of the base stations is used as the original point of a world coordinate system of the positioning system, the dental film machine is placed between the two base stations, a head mold in the dental film machine faces the base station used as the original point of the world coordinate system, and a Y axis of the tracker is parallel to a long axis of the tube and points to the head mold.

3. The ray-free dental X-ray periapical film virtual imaging method based on VR according to claim 1, characterized in that, in step S2, the teeth are scanned by using a Micro-Computer Tomography (Micro-CT) or Cone Beam Computer Tomography (CBCT) technology.

4. The ray-free dental X-ray periapical film virtual imaging method based on VR according to claim 1, characterized in that, in step S2, the tooth model comprises pulp and enamel, the material of the tooth shell model is set to be white, and the material of the pulp cavity model is set to be black.

5. The ray-free dental X-ray periapical film virtual imaging method based on VR according to claim 1, characterized in that, in step S3, the plurality of planes are added around the teeth to surround the teeth, and only a front opening is left to simulate the environment of an oral cavity.

6. The ray-free dental X-ray periapical film virtual imaging method based on VR according to claim 1, characterized in that, in step S4, the assignment of the acquired attitude matrix and the position data of the tracker is completed by using a publish-subscribe model, wherein a port for acquiring the attitude matrix and the position data of the tracker is used as a publisher, and a port where the virtual camera is located is used as a subscriber.

* * * * *